United States Patent [19]

Stabel Uwe et al.

[11] Patent Number: 5,128,490

[45] Date of Patent: Jul. 7, 1992

[54] ISOLATION OF TETRAHYDROFURAN FROM MIXTURES WHICH CONTAIN TETRAHYDROFURAN, 1,4-BUTANEDIOL, GAMMA-BUTYRO-LACTONE AND SUCCINIC ACID ESTERS

[75] Inventors: Stabel Uwe, Edingen-Neckarhausen; Hans-Juergen Gosch, Bad Durkheim; Rolf Fischer, Heidelberg; Wolfgang Harder, Weinheim; Claus Hechler, Mannheim, all of Fed. Rep. of Germany

[73] Assignee: Basf Aktiengesellschaft, Ludwigshafen, Fed. Rep. of Germany

[21] Appl. No.: 658,087

[22] Filed: Feb. 20, 1991

[30] Foreign Application Priority Data

Feb. 20, 1990 [DE] Fed. Rep. of Germany ....... 4005295

[51] Int. Cl.$^5$ ............................................ C07D 307/08
[52] U.S. Cl. ........................................ 549/509; 549/508
[58] Field of Search ........................... 549/508, 509

[56] References Cited

U.S. PATENT DOCUMENTS

| | | | |
|---|---|---|---|
| 4,094,887 | 6/1978 | Tanabe | 549/509 |
| 4,156,685 | 5/1979 | Tanabe et al. | 549/508 |
| 4,904,806 | 7/1990 | Hoelderich et al. | 549/509 |
| 4,912,236 | 3/1990 | Palm et al. | 549/509 |
| 4,940,805 | 7/1990 | Fischer et al. | 549/508 |
| 4,977,284 | 12/1990 | Suzuki et al. | 549/508 |

FOREIGN PATENT DOCUMENTS 1487200 9/1977 United Kingdom .

OTHER PUBLICATIONS

Chemical Abstracts, vol. 104 (1986), 131959h-Tetrahydrofuran.
Kotkar et al:J. Chem. Soc., Chem. Commun., 650 (1986).
Kotkar et al:J. Chem. Soc., Perkin Trans. I, 1749 (1988).
J. Chem. Soc. Perkin Trans. I, 1988, pp. 1749–1751.

*Primary Examiner*—C. Warren Ivy
*Assistant Examiner*—James H. Turnipseed
*Attorney, Agent, or Firm*—John H. Shurtleff

[57] ABSTRACT

A process is described for isolating tetrahydrofuran from mixtures containing tetrahydrofuran, 1,4-butanediol, -butyrolactone and succinic acid esters, in which the mixtures are heated to from 150° to 250° C. in the presence of phyllosilicates, the resultant tetrahydrofuran and water of reaction are removed from the reaction mixture by distillation, and the tetrahydrofuran is separated from the distillate.

10 Claims, No Drawings

ISOLATION OF TETRAHYDROFURAN FROM MIXTURES WHICH CONTAIN TETRAHYDROFURAN, 1,4-BUTANEDIOL, GAMMA-BUTYRO-LACTONE AND SUCCINIC ACID ESTERS

The present invention relates to a process for isolating tetrahydrofuran from mixtures which contain 1,4-butanediol, tetrahydrofuran, γ-butyrolactone and succinic acid esters and are produced on catalytic hydrogenation of maleic acid, succinic acid, fumaric acid, the esters of these acids, maleic anhydride or succinic anhydride in the presence of alcohols.

In the text below, the following abbreviations are used: MA=maleic acid, FA=fumaric acid, SA=succinic acid, MAA=maleic anhydride, SAA=succinic anhydride, THF=tetrahydrofuran, GBL=γ-butyrolactone, BD=1,4-butanediol, BuOH=n-butanol, DBSA=dibutyl succinate, POH=propanol and HB=high-boiling constituents.

Numerous processes have already been proposed for the catalytic hydrogenation of MAA. Since, as described, for example, in EP-A-304 696, this gives valuable intermediates, such as THF, GBL and BD, there has been considerable industrial interest in the hydrogenation of MAA. If the aim is to obtain the highest possible yield of THF, the overall yield of THF must be increased by cyclizing the BD in the mixture after separation. It is known to cyclize BD to give THF using acidic catalysts, such as sulfuric acid, phosphoric acid, acid metal oxides, such as $Al_2O_3$ and MgO, zeolites and acidic phyllosilicates. Thus, the method of, for example, J. Chem. Soc. Perkin Trans I, 1988, 1749–1751 converts BD into THF in a yield of 93% by heating for one hour at 160° C. in the presence of montmorillonite.

However, if the cyclization of BD is carried out starting from a mixture containing BD, GBL and succinic acid esters, BD is not converted completely into THF without loss of GBL and succinic acid esters. In order to avoid these problems, the catalyst would have to have a cyclization activity which is very high for cyclization in dilute solution in order to achieve complete conversions with small amounts of catalyst. On the other hand, in order to avoid losses of valuable product, the BD must not undergo any substantial reaction with GBL or with succinic acid esters under the influence of the acidic catalysts. Thus, in the cyclization of the above-mentioned mixtures at 180° C. using sulfuric acid as catalyst, considerable amounts of BD, GBL and succinic acid derivatives are converted into a high-boiling oligomer mixture which solidifies at low temperature to give a waxy material. The same result is also observed in cyclization using alumina as catalyst. In cyclization using magnesium oxide, transesterification of succinic acid esters with BD is observed, considerably reducing the yield of THF.

It is an object of the present invention to find a process which allows the cyclization of BD in mixtures of BD, GBL and succinic acid esters to be carried out with the aim of highest possible conversion into THF while avoiding losses in the yield of GBL and succinic acid esters.

It is a further object of the present invention to completely separate the catalyst from the valuable products in a simple manner after the cyclization.

We have found that these objects are achieved by a process for isolating THF from mixtures produced on catalytic hydrogenation of MA, SA, FA, the esters of these acids, MAA or SAA in the presence of alcohols and containing THF, BD, GBL, succinic acid esters and the alcohol employed, by removing THF, the alcohols and water from the mixtures by distillation, then heating the mixtures to from 100° to 250° C. in the presence of phyllosilicates, removing the resultant tetrahydrofuran and water of reaction from the reaction mixture by distillation, and separating the tetrahydrofuran from the distillate.

Surprisingly, the process according to the invention achieves complete reaction of BD present in the mixture under mild conditions with a selectivity of around 100%. The target product solution of GBL and succinic acid esters obtained when cyclization is complete is of low viscosity, in contrast to the product solution obtained if the cyclization is carried out using sulfuric acid or alumina as catalyst. Significant losses of GBL and succinic acid esters are not observed. It is advantageous that the catalyst can easily be separated from the low-viscosity solution, even at room temperature, by filtration or one-step evaporation of the target products. If desired, the catalyst can be re-used.

The starting mixtures employed are those produced on catalytic hydrogenation of MA, SA, FA, the esters of these acids, MAA or SAA in the presence of alcohols, such as methanol, ethanol, propanol, isopropanol or the various isomeric butanols, the use of these butanols, in particular n-butanol, being preferred, and containing THF, BD, GBL, succinic acid esters, such as DBSA, and the alcohols employed. In addition, the mixtures may contain BuOH, $H_2O$ and small amounts of POH and HB. Examples of starting mixtures which can be used are the reaction mixtures produced on hydrogenation of MAA as described in EP-A-304 696. They have, for example, the following composition:

THF from 0.1 to 15% by weight, preferably from 1 to 7% by weight
$H_2O$ from 3 to 15% by weight, preferably from 7 to 9% by weight
POH from 0.1 to 5% by weight, preferably from 0.5 to 1% by weight
BuOH from 20 to 80% by weight, preferably from 50 to 60% by weight
DBSA from 1 to 20% by weight, preferably from 3 to 8% by weight
BD from 10 to 30% by weight, preferably from 19 to 21% by weight
GBL from 0.5 to 10% by weight, preferably from 1 to 5% by weight The cyclization of BD in the starting mixtures is carried out at from 100° C. to 250° C., preferably at from 150° C. to 190° C., in the presence of phyllosilicates, which are silicates with a layer structure, such as aluminum silicates or magnesium silicates of the montmorillonite, bentonite or bleaching earth type. Particularly suitable phyllosilicates, for example montmorillonites and bentonites, are those which are doped with hydrogen ions or with elements of the third main group of the Periodic Table, in particular with boron, aluminum, gallium and/or indium, the use of aluminum-doped montmorillonites being particularly preferred. The phyllosilicates are employed in amounts of from 0.05 to 1% by weight, based on the BD.

If the abovementioned THF-containing starting mixtures, produced on catalytic hydrogenation of MAA, are used, it is advisable to free them from traces of catalyst constituents washed out of the hydrogenation catalyst. To this end, the hydrogenation mixture is demineralized using a commercially available, continuous cation exchanger at up to 50° C. before the cyclization. The same purpose is achieved by one-step evaporation and condensation of the hydrogenation products. This means that the cyclization can be carried out using small amounts of catalyst. Before treatment with the phyllosilicate, the low-boiling components, such as THF, the alcohols, for example the BuOH, and water are removed by distillation. This is achieved using, for example, a continuous distillation column, from which the low-boiling components are removed at the head at, for example, from 0.1 to 2 bar. The bottom product, which contains GBL, DBSA, BD and HB, is reacted, for example, either batchwise or continuously with the catalyst in a stirred reaction in order to cyclize the BD. The THF formed is constantly removed by distillation together with the water of reaction and expediently combined with the low-boiling distillate. The pure THF is separated off by conventional methods, for example by fractional distillation. When reaction of the BD is complete, the catalysts are separated off by filtration or one-step evaporation. The GBL/DBSA mixture which remains can be recycled into the MAA hydrogenation reaction. Complete recycling of the target products into the hydrogenation step converts a process for the preparation of BD into a process which gives THF in high selectivity and overall yield. The process permits particularly economical isolation of THF from said reaction mixtures while avoiding work-up of BD.

EXAMPLE 1

Batch cyclization in a stirred reactor

Hydrogenation of MAA carried out in accordance with Example 8 of EP-A-304 696 gives a reaction mixture having the following composition:

| THF | 6.4% by weight |
| --- | --- |
| $H_2O$ | 8.6% by weight |
| POH | 0.5% by weight |
| BuOH | 58.3% by weight |
| DBSA | 4.2% by weight |
| BD | 14.0% by weight |
| GBL | 1.1% by weight |
| By-products | 6.9% by weight |

From 1 to 3 l of the mixture per hour were pumped through a glass column (diameter 50 mm, length 600 mm) packed with 1 l of cation exchanger obtainable under the trade name Amberlyst ® 15 in order to continuously remove cations. The column was operated at from 20° to 60° C. In order to avoid bleeding of sulfur constituents during the demineralization, the ion exchanger was treated with n-butanol at 60° C. for 24 hours before being used.

In order to continuously remove the low-boiling components, the demineralized mixture was pumped into a column whose bottom was simultaneously used as reactor for continuous cyclization (metering of the catalyst into the bottom).

In the case of a batchwise reaction, the bottom product, free from low-boiling components, was transferred into a batch stirred reactor equipped with distillation bridge, 0.4% by weight of the catalyst, based on the BD present therein, was added, and the cyclization reaction was carried out.

The stripping part of the column for removing the low-boiling components comprised a bubble-cap tray column, heated approximately to the reaction temperature, having 5 trays in order to minimize remixing of the high-boiling constituents with low-boiling components.

The rectifying part comprised a column (diameter 50 mm, length 400 mm) with Sulzer wire-web packing. The column was operated at a reflux ratio of from 0.5 to 1.0 (bottom temperature 170°–190° C., atmospheric pressure).

After distillative removal of the low-boiling components, the bottom product was treated, for cyclization thereof, with 0.4% by weight, based on the BD present therein, of an aluminum-doped montmorillonite, and this mixture was heated to 180° C. The resultant THF and water of reaction were removed continuously by distillation. The reaction was complete after 1.5 hours (subsidence of boiling). The bottom product obtained after this reaction had a low viscosity, even at room temperature, and contained GBL and DBSA as principal constituents. The distillate had the following composition:

| Water | 10.0% by weight |
| --- | --- |
| GBL | 1.5% by weight |
| BuOH | 3.0% by weight |
| THF | 85.5% by weight |

The cyclization selectivity was 100% at a 98% conversion of the butanediol.

The catalyst used was prepared as follows:

80 g of montmorillonite (powdered) were added to a solution of 480 g of $Al(NO_3)_3.9H_2O$ in 720 g of $H_2O$. The mixture was stirred at 80° C. for 4 hours, and the doped montmorillonite was then filtered off, washed until free of nitrate and dried at from 100° to 200° C. in a drying oven. The powder, which bakes together in some cases, was comminuted in the mortar. The aluminum nitrate used in excess can be re-used for further doping.

EXAMPLE 2

Continuous cyclization in a stirred reactor

Two reaction mixtures obtainable by the process described in EP-A-304 696 were employed. The hydrogenation mixtures had the following composition: Composition of the hydrogenation mixtures (in % by weight):

|  | Hydrogenation mixture I before cyclization | Products |
| --- | --- | --- |
| THF | 6.4 | 18.3 |
| $H_2O$ | 8.6 | 11.7 |
| POH | — | — |
| BuOH | 58.3 | 60.7 |
| DBSA | 4.2 | 3.7 |
| BD | 14.0 | 0.1 |
| GBL | 1.1 | 2.0 |
| Others | 7.4 | 3.6 |
| Total weight | 8291 g | 8272 g |

Selectivity = 105%
Conversion of BD = 99.1%
Throughput = 1500 g/h

The selectivity at 105% is attributable to the fact that the hydrogenation mixture I contained BD-equivalent compounds, such as oligomeric ethers of BD, which had not been covered in the analysis of hydrogenation mixture I and are converted during cyclization to give THF.

| | Hydrogenation mixture II before cyclization | Products |
|---|---|---|
| THF | 1.7 | 17.0 |
| H$_2$O | 7.2 | 11.6 |
| POH | 0.2 | — |
| BuOH | 56.8 | 59.6 |
| DBSA | 6.7 | 6.7 |
| BD | 19.1 | 0.1 |
| GBL | 2.2 | 1.8 |
| Others | 5.3 | 3.4 |
| Total weight | 5576 g | 5531 g |

Selectivity = 100%
Conversion of BD = 99.6%
Throughput = 1000 g/h

From 1000 to 1500 g of the respective hydrogenation mixtures of compositions I and II were demineralized as described in Example 1, and the low-boiling components were distilled off. The bottom product was cyclized at from 180° to 190° C. in the bottom of the column at a reaction volume of from 0.7 to 1.6 l, with continuous addition of from 0.2 to 0.6% by weight of the catalyst described in Example 1, based on the BD employed. The THF and water of reaction formed with vigorous boiling were removed continuously from the stirred reactor by distillation and combined with the low-boiling component distillate. The mean yield of THF is 99.9%, based on the BD present in the hydrogenation mixtures. The bottom product, discharged continuously, had low viscosity, even at room temperature, and contained GBL and DBSA as the principal constituents. The target products were recycled into the hydrogenation of MAA after removing the catalyst by filtration or one-step evaporation.

EXAMPLES 3 TO 6

In Examples 3 to 6, the demineralized hydrogenation product, free of low-boiling components, also employed in Example 1 was cyclized by the process of Example 1 using various catalysts and various reaction times (RT). The cyclization catalysts used were γ-aluminum oxide (comparative example), Tonsil®, an acid-activated calcium bentonite from Süd-Chemie, and an acid-activated, i.e., hydrogen ion-doped, montmorillonite. The results achieved with respect to selectivity (SEL), conversion and consistency of the cyclization product are listed in the table below, together with the result from Example 1:

| Example No. | Catalyst | Reaction temperature °C. | SEL % | Conversion % | RT h | Consistency of the cyclization product after the reaction |
|---|---|---|---|---|---|---|
| 3 | γ-Al$_2$O$_3$ | 238 | 57 | 68 | 5 | high viscosity |
| 4 | Tonsil® | 180 | 97 | 97 | 4 | low viscosity |
| 5 | Tonsil® | 180 | 100 | 97 | 7 | low viscosity |
| 6 | Montmorillonite, H$^+$-doped | 180 | 84 | 98 | 4 | low viscosity |
| 1 | Montmorillonite, Al$^{3+}$-doped | 180 | 100 | 98 | 1.5 | low viscosity |

We claim:

1. A process for isolating tetrahydrofuran from a mixture produced on catalytic hydrogenation of maleic acid, succinic acid, fumaric acid, the esters of these acids, maleic anhydride or succinic anhydride in the presence of alcohols and containing tetrahydrofuran, 1,4-butanediol, γ-butryolactone, succinic acid esters and the alcohol employed, which comprises removing tetrahydrofuran, the alcohols and water from the mixture by distillation, then cyclizing the 1,4-butanediol to form tetrahydrofuran by heating the mixture to from 100° to 250° C. in the presence of a phyllosilicate, removing the resultant tetrahydrofuran and water of reaction from the reaction mixture by distillation, and separating the tetrahydrofuran from the distillate.

2. A process as claimed in claim 1, wherein mixtures are employed which are produced on catalytic hydrogenation of maleic anhydride in the presence of butanols and contain tetrahydrofuran, butanol, propanol, 1,4-butanediol, γ-butyrolactone, dibutyl succinate and water, the treatment of the mixture with the phyllosilicate being preceded by removal of tetrahydrofuran, propanol, butanol and water by distillation.

3. A process as claimed in claim 2, wherein the mixtures are freed from hydrogenation catalyst constituents, present in traces, before treatment with the phyllosilicate.

4. A process as claimed in claim 1, using a small catalytic amount of the phyllosilicate.

5. A process as claimed in claim 1, wherein the phyllosilicate is used in an amount of from 0.05 to 1% by weight, based on the 1,4-butanediol.

6. A process as claimed in claim 1, wherein the cyclization step is carried out at a temperature of from 150° to 190° C.

7. A process as claimed in claim 6, wherein the phyllosilicate is selected from the group consisting of montmorillonites, bentonites and bleaching earths.

8. A process as claimed in claim 6, wherein the phyllosilicate is selected from the group consisting of the montmorillonite and bentonite types which have been doped with hydrogen ions or elements of the third main group of the Periodic Table.

9. A process as claimed in claim 8, wherein the phyllosilicate has been doped with an element selected from the group consisting of boron, aluminum, gallium, indium and mixtures thereof.

10. A process as claimed in claim 8, wherein an aluminum-doped montmorillonite is used as the phyllosilicate.

* * * * *

UNITED STATES PATENT AND TRADEMARK OFFICE
CERTIFICATE OF CORRECTION

PATENT NO. : 5,128,490
DATED : July 7, 1992
INVENTOR(S) : Stabel et al.

It is certified that error appears in the above-identified patent and that said Letters Patent is hereby corrected as shown below:

On the title page:

Item [75]: The inventors should read as follows:

-- Stabel et al. --

After [75] Inventors:, correct the name of the first inventor to read: -- Uwe Stabel --.

IN THE ABSTRACT:

Line 3, after "butanediol", change " -butyrolactone" to -- γ-butyrolactone --.

Signed and Sealed this

Tenth Day of August, 1993

Attest:

MICHAEL K. KIRK

*Attesting Officer*  *Acting Commissioner of Patents and Trademarks*